United States Patent [19]

Swanson

[11] Patent Number: 5,605,543
[45] Date of Patent: Feb. 25, 1997

[54] CATHETER HAVING SHAFT OF VARYING STIFFNESS

[75] Inventor: William J. Swanson, St. Paul, Minn.

[73] Assignee: Schneider (USA) Inc., Plymouth, Minn.

[21] Appl. No.: 594,355

[22] Filed: Jan. 30, 1996

Related U.S. Application Data

[63] Continuation of Ser. No. 374,388, Jan. 17, 1995, abandoned, which is a continuation of Ser. No. 209,342, Mar. 10, 1994, abandoned.

[51] Int. Cl.⁶ .................................................. A61M 29/00
[52] U.S. Cl. .............................................. 604/96; 604/194
[58] Field of Search ........................... 604/96, 102, 280, 604/264; 606/192, 194

[56] References Cited

U.S. PATENT DOCUMENTS

| | | |
|---|---|---|
| 4,323,071 | 4/1982 | Simpson et al. . |
| 4,547,193 | 10/1985 | Rydell ...................................... 604/282 |
| 4,646,742 | 3/1987 | Packard et al. ........................ 128/344 |
| 4,739,768 | 4/1988 | Engelson . |
| 4,838,268 | 6/1989 | Keith et al. . |
| 4,906,241 | 3/1990 | Noddin et al. . |
| 4,917,088 | 4/1990 | Crittenden . |
| 4,921,483 | 5/1990 | Wijay et al. . |
| 4,940,062 | 7/1990 | Hampton et al. . |
| 4,943,278 | 7/1990 | Euteneuer et al. . |
| 4,946,466 | 8/1990 | Pinchuk et al. . |
| 4,960,410 | 10/1990 | Pinchuk . |
| 4,976,690 | 12/1990 | Solar et al. . |
| 4,976,720 | 12/1990 | Machold et al. . |
| 4,998,917 | 3/1991 | Gaiser et al. . |
| 4,998,923 | 3/1991 | Samson et al. ........................ 606/194 |
| 5,032,113 | 7/1991 | Burns . |
| 5,035,705 | 7/1991 | Burns . |
| 5,047,045 | 9/1991 | Arney et al. . |
| 5,085,636 | 2/1992 | Burns . |
| 5,100,381 | 3/1992 | Burns . |
| 5,104,376 | 4/1992 | Crittenden . |
| 5,154,725 | 10/1992 | Leopold . |
| 5,156,594 | 10/1992 | Keith . |
| 5,156,595 | 10/1992 | Adams . |
| 5,176,637 | 1/1993 | Sagae . |
| 5,180,376 | 1/1993 | Fischell ................................. 604/282 |
| 5,195,971 | 3/1993 | Sirhan . |
| 5,195,978 | 3/1993 | Schiffer . |
| 5,195,989 | 3/1993 | Euteneuer . |
| 5,217,482 | 6/1993 | Keith . |
| 5,242,394 | 9/1993 | Tremulis . |
| 5,250,069 | 10/1993 | Nobuyoshi et al. . |
| 5,256,144 | 10/1993 | Kraus et al. ............................ 604/96 |
| 5,322,064 | 6/1994 | Lundquist .............................. 128/642 |
| 5,322,505 | 6/1994 | Krause et al. .......................... 604/24 |
| 5,437,288 | 8/1995 | Schwartz et al. ..................... 128/772 |

FOREIGN PATENT DOCUMENTS

| | | |
|---|---|---|
| 0376132A1 | 7/1990 | European Pat. Off. . |
| 0380873 | 8/1990 | European Pat. Off. . |
| 0405831 | 1/1991 | European Pat. Off. . |
| 0513818 | 11/1992 | European Pat. Off. . |
| 0608853A2 | 8/1994 | European Pat. Off. . |
| 4104092 | 8/1991 | Germany . |
| 9108014 | 6/1991 | WIPO . |
| 9302733 | 2/1993 | WIPO . |
| 9304722 | 3/1993 | WIPO . |
| 9315786 | 8/1993 | WIPO . |
| 9320882 | 10/1993 | WIPO . |

OTHER PUBLICATIONS

PCT International Search Report in PCT/IB95/00075 dated Apr. 28, 1995, together with Notification and one-page annex.

Primary Examiner—Corrine M. McDermott
Attorney, Agent, or Firm—Lawrence C. Akers; Peter C. Richardson; Philip C. Strassburger

[57] ABSTRACT

A medical device such as a catheter is described having a stiff, preferably metallic, proximal tube. The distal portion of the proximal tube may have a plurality of perforations or slots formed therein to increase its flexibility. This provides a smooth transition between the relatively stiff proximal tube and a more flexible distal polymeric tube.

22 Claims, 9 Drawing Sheets

CATHETER HAVING SHAFT OF VARYING STIFFNESS

This is a continuation, of application Ser. No. 08/374,388, filed on Jan. 17, 1995, now abandoned, which is a continuation of application Ser. No. 08/209,342, filed Mar. 10, 1994, now abandoned.

BACKGROUND OF THE INVENTION

This invention relates to an improved catheter, more particularly a balloon catheter for use in angioplasty. This invention is even more particularly adapted for use as a balloon dilatation catheter in percutaneous transluminal coronary angioplasty (PTCA). A PTCA procedure is used to dilate the stenosed region of a diseased coronary blood vessel. In a typical PTCA procedure, a guide catheter is introduced in a peripheral artery, such as the femoral artery, and advanced through the aorta until the distal end of the guide catheter is engaged with the coronary ostium for the coronary artery to be treated. Next a balloon dilatation catheter is introduced over a guidewire which has been introduced through the guide catheter. The guidewire is advanced past the distal end of the guide catheter within the lumen of the diseased vessel and manipulated across the region of the stenosis. The balloon dilatation catheter is then advanced past the distal end of the guide catheter over the guidewire until the balloon is positioned across the stenotic lesion. The balloon is inflated by supplying a fluid under pressure to the balloon through an inflation lumen in the catheter. Inflating the balloon stretches the diseased artery to reestablish acceptable blood flow through the artery.

A typical over the wire balloon dilatation catheter has two lumens extending through substantially the entire length of the catheter. One lumen is used to pass the guidewire through the catheter and extends from a proximal guidewire port to a distal guidewire port located distal of the balloon. The other lumen is used to inflate and deflate the balloon and extends from a proximal inflation port adjacent to the proximal end of the catheter to a distal inflation port which is in communication with the balloon cavity.

A typical rapid exchange balloon dilatation catheter has a single inflation lumen extending from the proximal end of the catheter to the distal inflation port which is in communication with the balloon cavity. The guidewire lumen extends through only the most distal portion of the catheter from a proximal guidewire port, which is proximal of the balloon but distal to the proximal end of the catheter, to a distal guidewire port in the distal end of the catheter. This configuration facilitates the maintenance of the location of the guidewire across the stenosis during catheter exchange.

A typical fixed-wire balloon dilatation catheter has a single lumen shaft that extends from the proximal end of the catheter to the proximal end of the balloon. A wire is fixed in the catheter and extends past the distal end of the balloon which is connected thereto. The fixed-wire acts as the guidewire to steer the catheter so that a separate guidewire is not needed.

In order for a balloon dilatation catheter optimally to perform its function in an angioplasty procedure, the catheter should have a small profile, a flexible distal portion and a stiff proximal portion. The small profile allows the catheter to be inserted into small arteries. A flexible distal portion allows that part of the catheter to pass through the tortuous, tight curvatures of the vasculature. In addition, a stiff proximal portion gives the catheter "pushability", i.e. transmission of longitudinal force along the catheter, so a physician can push the catheter through the vascular system and the stenosis. Finally the transition between the stiff proximal portion and the flexible distal portion should be smooth and should avoid areas of high stress concentration.

Balloon dilatation catheters currently on the market attempt to achieve these goals with varying degrees of success. However, none has heretofore provided such an optimum combination of features.

Therefore it would be desirable to provide a balloon dilatation catheter that has a small profile.

It would also be desirable to provide a balloon dilatation catheter having a flexible distal portion.

It would be further desirable to provide a balloon dilatation catheter having a stiff proximal portion.

It would be yet further desirable to provide a balloon dilatation catheter that has a smooth transition from a stiff proximal portion to a flexible distal portion which avoids areas of high stress concentration.

SUMMARY OF THE INVENTION

These and other objects of the invention are achieved by a balloon dilatation catheter having a stiff proximal tube preferably formed from metal. The use of metal helps to provide a balloon dilatation catheter with a small profile. The metal used for the proximal tube can be made from, for example, stainless steel hypotube, a superelastic alloy such as nitinol, nickel and its alloys, or titanium and its alloys or any other biocompatible metal. The distal portion or transition zone of the metallic proximal tube has one or more perforations or slots formed therein to increase the flexibility of the distal portion. This increased flexibility of the distal portion of the proximal tube facilitates the transition from the relatively stiff portion to a more flexible portion and avoids a region of high stress concentration. Preferably the transition zone is formed with a plurality of discrete perforations arranged generally in rows. The perforations in one row are offset from the perforations in an adjacent row. In addition, preferably the perforations in one row extend at least partially into the space between the perforations in an adjacent row.

Although the present invention has particular applicability to balloon dilatation catheters, it is also applicable to other medical devices having the same requirements of a stiff proximal portion, a flexible distal portion and a smooth transition between the stiff proximal portion and the flexible distal portion to avoid areas of high stress concentration. For example, this invention could be used as part of a stent delivery catheter, guide catheter or diagnostic catheter.

BRIEF DESCRIPTION OF THE DRAWINGS

The above and other objects and advantages of this invention will become apparent upon consideration of the following detailed description taken in conjunction with the accompanying drawings, in which like reference characters refer to like parts throughout and in which.

DETAILED DESCRIPTION OF THE INVENTION

Figure 1:
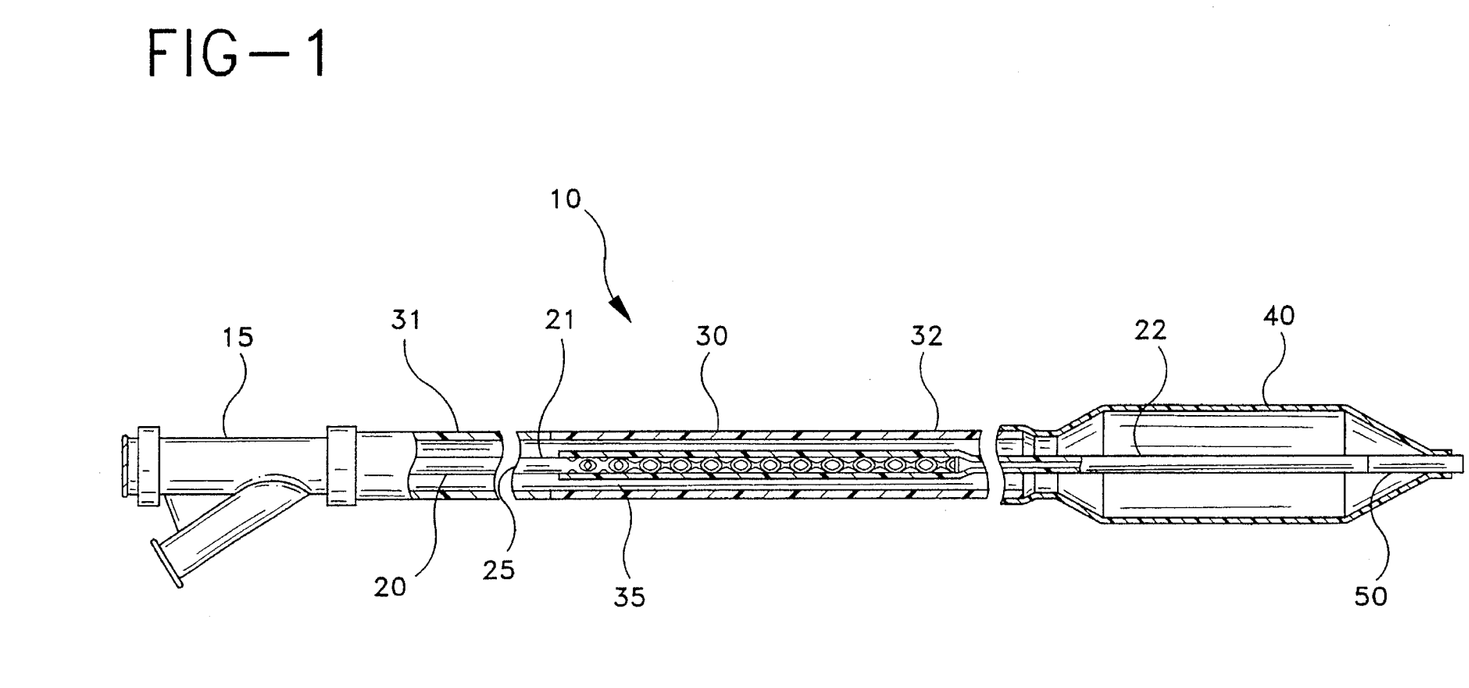
FIG. 1 is a partial section side elevation view of one embodiment of an over the wire balloon dilatation catheter of this invention.

The balloon dilatation catheter 10 depicted in FIG. 1 has a coaxial tube design with an inner guidewire tube 20 surrounded by an outer inflation tube 30. The lumen defined by guidewire tube 20 is the guidewire lumen 25. The annular space formed between guidewire tube 20 and inflation tube 30 defines the inflation lumen 35. The proximal end of guidewire tube 20 and inflation tube 30 are mounted in a standard manifold 15. A balloon 40 is mounted to the distal end of guidewire tube 20 and inflation tube 30. A soft bumper tip 50 can be affixed to the distal end of guidewire tube 20. Bumper tip 50 can be formed from a relatively soft polymeric material such as polyethylene with a flex modulus of between 5000 psi and 100,000 psi (34.47 MPa and 689.48 MPa). (It is to be understood that all of the values for pressure and dimension provided herein relate to the use of the subject invention in a balloon dilatation catheter adapted for use in PTCA procedures. It is also to be understood that these values can vary depending on the particular application for the invention without deviating from the scope and spirit of the invention.) Bumper tip 50 minimizes the chances of vascular trauma when balloon catheter 10 is maneuvered through the vascular system to the treatment site.

Inflation tube 30 may be a single tube piece or may be formed from multiple pieces as shown in FIG. 1. Using a single tube piece for inflation tube 30 facilitates manufacturability, improves reliability and masks the transition point of guidewire tube 20 where multiple tube pieces are used for guidewire tube 20. If multiple tube pieces are used for inflation tube 30, a proximal inflation tube 31 and a distal inflation tube 32 connected at its proximal end to the distal end of proximal inflation tube 31 are used. By using multiple sections, the characteristics of proximal inflation tube 31 and distal inflation tube 32 can be tailored to the requirements of catheter 10. Of course, where multiple sections are used for both inflation tube 30 and guidewire tube 20, distal inflation tube 32 could be formed from a single tube having a bilumen configuration, where the lumens are side by side rather than coaxial. In addition, the relative locations between the bonds in inflation tube 30 and guidewire tube 20 could vary so that they are radially aligned or one is proximal or distal to the other. As shown in FIG. 1, the bond connecting the multiple pieces of inflation tube 30 is proximal to the area of the bond connecting the multiple pieces of guidewire tube 20.

Inflation tube 30 should be flexible and lubricous and should be able to withstand pressures in the range of up to about 20 atmospheres (294 psi) (2.03 MPa) which is the maximum inflation pressure that may be used to inflate balloon 40. Suitable materials for inflation tube 30 include high density polyethylene, polyimide, and various other polymeric materials. These materials preferably have a flex modulus in the range of 10,000 psi to 500,000 psi (68.85 MPa to 3447.36 MPa). In addition, a wall thickness in the range of 0.001 inches to 0.005 inches (0.025 mm to 0.13 mm) and an outer diameter in the range of 0.030 inches to 0.050 inches (0.76 mm to 1.27 mm) should be used for inflation tube 30 to minimize the profile of catheter 10.

If multiple tube pieces are used for inflation tube 30, proximal inflation tube 31 should have the characteristics of inflation tube 30 described above. Distal inflation tube 32, like proximal inflation tube 31, should be able to withstand pressures of up to 20 atmospheres (294 psi) (2.03 MPa). However, distal inflation tube 32 should be more flexible than proximal inflation tube 31 to allow the distal portion of catheter 10 to be guided through the tortuous passages of the vasculature. Suitable material for distal inflation tube 32 includes polyethylene or other polymers having a flex modulus in the range of 10,000 psi to 500,000 psi (68.94 MPa to 3447.4 MPa). Again the wall thickness of distal inflation tube 32 should be in the range of 0.001 inches to 0.005 inches (0.025 mm to 0.13 mm) and distal inflation tube 32 should have an outer diameter in the range of 0.030 inches to 0.050 inches (0.76 mm to 1.27 mm) to minimize the profile of catheter 10.

Where multiple tube pieces are used for inflation tube 30, the distal end of proximal inflation tube 31 is bonded to the proximal end of distal inflation tube 32 by heat. Although heat bonding is preferred, any suitable bonding technique, such as the use of a chemical adhesive, could also be used.

The proximal neck of balloon 40 is bonded adjacent the distal end of distal inflation tube 32. Alternatively, if a single tube piece is used, the proximal neck of balloon 40 is bonded adjacent the distal end of inflation tube 30. Again, heat bonding is preferred although other suitable bonding techniques can be used.

Although guidewire tube 20 may be a single tube piece, it is preferably formed from multiple pieces. Preferably a proximal guidewire tube 21 and a distal guidewire tube 22, having its proximal end connected to the distal end of proximal guidewire tube 21, are used. This multisection arrangement allows the characteristics of proximal guidewire tube 21 and distal guidewire tube 22 to vary to meet the needs of catheter 10. Proximal guidewire tube 21 is preferably stiff while distal guidewire tube 22 is preferably flexible.

In order to provide sufficient stiffness to proximal guidewire tube 21 so that the resulting catheter 10 has adequate pushability, proximal guidewire tube 21 is formed from a metal such as stainless steel hypotube, a superelastic alloy such as nitinol, nickel and its alloys or titanium and its alloys or any other biocompatible metal. This material provides proximal guidewire tube 21 with longitudinal stiffness, yet allows proximal guidewire tube 21 to have a wall thickness in the range of 0.001 inches to 0.005 inches (0.025 mm to 0.13 mm) and an outer diameter in the range of 0.018 inches to 0.035 inches (0.46 mm to 0.89 mm) which minimizes the profile of catheter 10, maximizes the size of inflation lumen 35 and still allows a guidewire to pass through guidewire lumen 25. Other stiff materials could also be used for proximal guidewire tube 21. Other suitably stiff materials include polyimide and polyether ether ketone (PEEK).

On the other hand, distal guidewire tube 22 should be flexible to track a guidewire through the tortuous vasculature. Distal guidewire tube 22 may be made from polyethylene and other polymers having a flex modulus in the range of 10,000 psi to 500,000 psi (68.84 MPa to 3447.3 MPa). In addition, the wall thickness of distal guidewire tube 22 should be in the range of 0.001 inches to 0.005 inches (0.025 mm to 0.13 mm) and an outer diameter in the range of 0.018 inches to 0.03 inches (0.046 mm to 0.076 mm). As discussed above, distal guidewire tube 22 could be formed from a tube having a bilumen configuration rather than being part of a coaxial tube arrangement where multiple tube pieces are used for inflation tube 30. The proximal end of distal guidewire tube 22 is preferably placed against the distal end of proximal guidewire tube 21 in abutting relationship. A sleeve formed of the same material as distal guidewire tube 22 is placed over the distal portion of proximal guidewire tube 21 and the proximal portion of distal guidewire tube 22. This sleeve is adhered to the outer surface of proximal guidewire tube 21 and distal guidewire tube 22 by a chemical adhesive and/or heat bonding. Alternatively, the proximal portion of distal guidewire tube 22 can be placed over or inside the distal portion of proximal guidewire tube 21 and adhered to the outer or inner surface of proximal guidewire tube 21.

Figure 2:
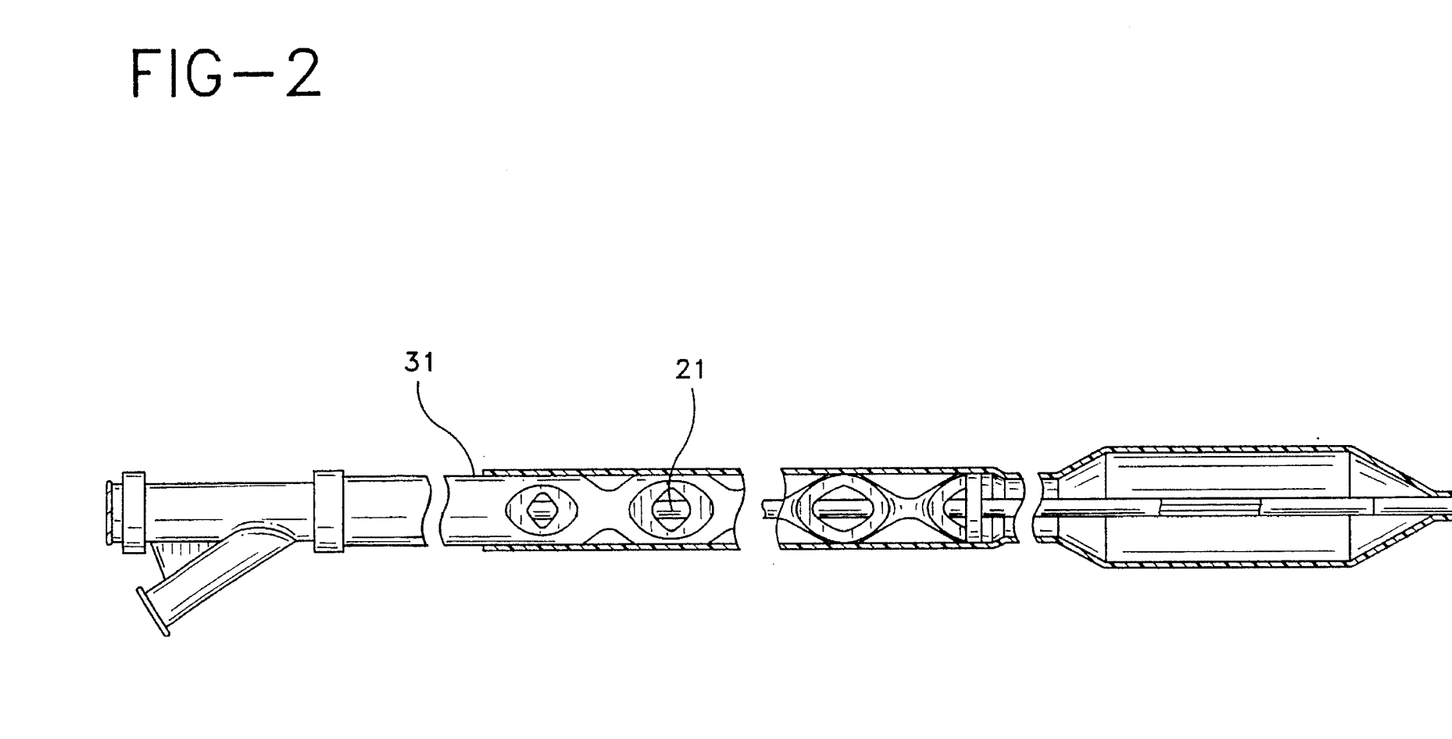
FIG. 2 is a partial section side elevation view of a second embodiment of an over the wire balloon dilatation catheter of this invention.

Although balloon dilatation catheter 10 is described above as having a stiff proximal guidewire tube 21, preferably formed from metal, it is also possible to have proximal inflation tube 31 formed from a stiff material, preferably metal. See FIG. 2. In such a case, proximal inflation tube 31 would have the properties and characteristics described above for proximal guidewire tube 21 and, conversely, proximal guidewire tube 21 would have the properties and characteristics described above for proximal inflation tube 31. It is important to note, however, that if proximal inflation tube 31 is formed from metal, the stiffness of the resulting catheter will be substantially greater than where proximal guidewire tube 21 is formed from metal. This results from the increased size of the metal tube used. In certain circumstances, this substantial increase in stiffness would be undesirable.

Figure 3:
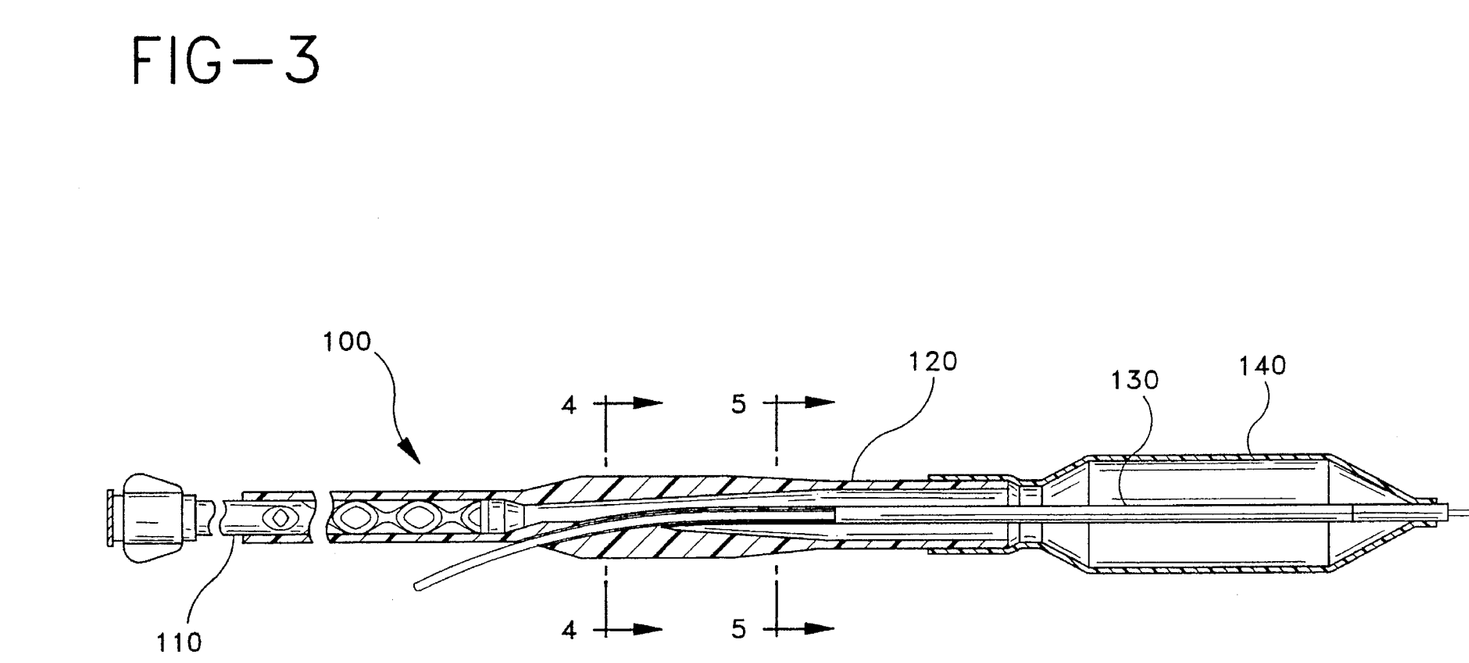
FIG. 3 is a partial section side elevation view of a third embodiment of a rapid exchange balloon dilatation catheter of this invention.
Figure 4:
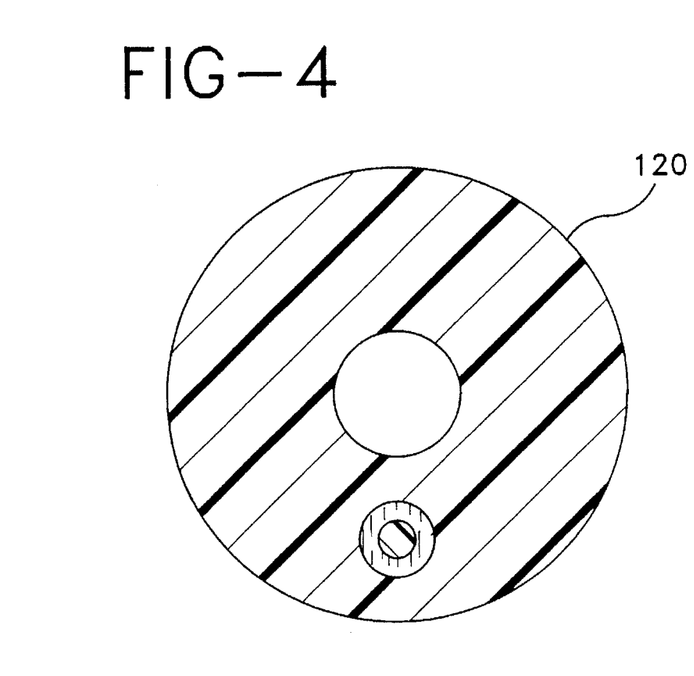
FIG. 4 is a sectional view taken along line 4—4 of FIG. 3.
Figure 5:
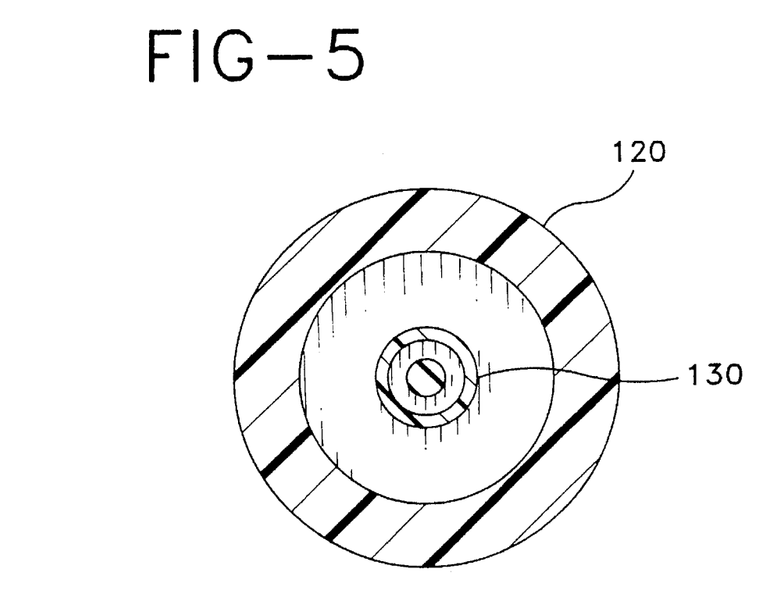
FIG. 5 is a sectional view taken along line 5—5 of FIG. 3.

In addition, the balloon dilatation catheter could have a rapid exchange configuration as shown in FIG. 3. Such a rapid exchange balloon dilatation catheter 100 has a proximal single lumen shaft 110 and a stem 120 affixed to the distal end of proximal shaft 110, which together define the inflation lumen. In addition, a short guidewire tube 130 which has a coaxial arrangement with stem 120 can be heat bonded to stem 120 to provide the configuration shown. Alternatively, the stem and guidewire tube could be formed from a single bilumen tube piece that defines both the distal portion of the inflation lumen and the entire guidewire lumen that extends through the balloon 140. The proximal neck of balloon 140 is bonded to stem 120 and the distal neck of balloon 140 is bonded to guidewire tube 130. As with balloon catheter 10, a soft bumper tip can be affixed to the distal end of guidewire tube 130. In a balloon dilatation catheter of this configuration, proximal shaft 110 is formed of a stiff material, preferably metal.

Figure 9:
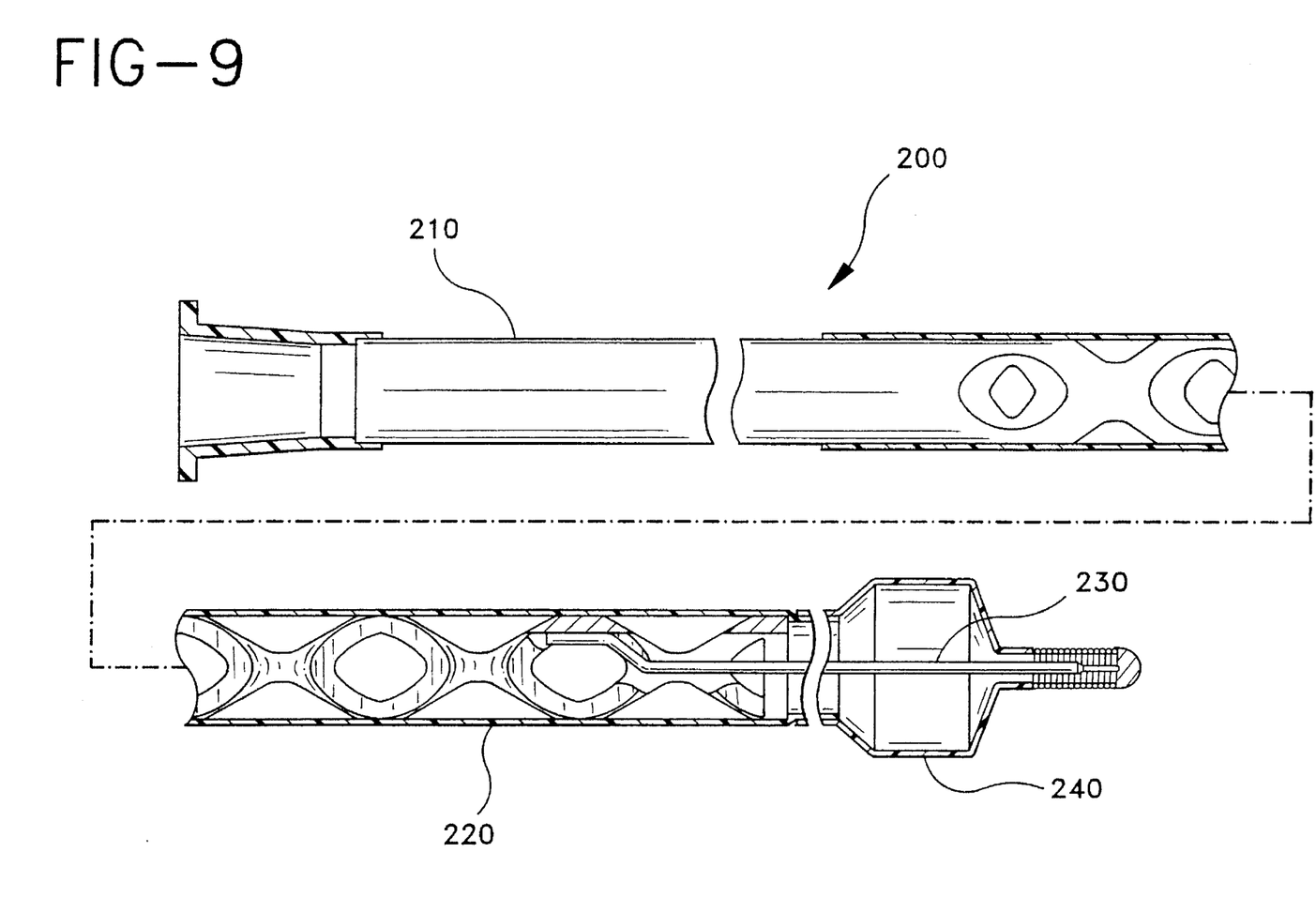
FIG. 9 is a partial section side elevation view of a fourth embodiment of a fixed-wire balloon dilatation catheter of this invention.

Alternatively, the balloon dilatation catheter could be of the fixed-wire type. See FIG. 9. Such a fixed-wire catheter 200 has a proximal single lumen shaft 210 and a stem 220 affixed to the distal end of proximal shaft 210, which together define the inflation lumen. A wire 230 is fixedly attached to catheter 200 and extends through the balloon 240. In the embodiment shown, wire 230 is bonded to proximal shaft 210. The proximal neck of balloon 240 is bonded to stem 220 and the distal neck of balloon 240 is bonded to wire 230. In the balloon dilatation catheter of this configuration, proximal shaft 210 is formed from a stiff material, preferably metal.

Although the present invention has particular applicability to balloon dilatation catheters, it is also applicable to other medical devices having the same requirements of a stiff proximal portion, a flexible distal portion and a smooth transition between the stiff proximal portion and the flexible distal portion to avoid areas of high stress concentration. For example, this invention could be used as part of a stent delivery catheter, guide catheter or diagnostic catheter.

Regardless of whether the stiff, preferably metallic, tube is used as proximal inflation tube 31 or proximal guidewire tube 21 in an over the wire catheter 10, as proximal shaft 110 in a rapid exchange catheter 100, as proximal shaft 210 in a fixed-wire catheter 200 or as a proximal tube in some other medical device, the transition between the stiff, preferably metallic, tube and the distal more flexible tube presents an abrupt change in the hardness and flexibility of the assembly. Unless properly designed, this transition could become the location for kinking or other catastrophic failure of the device. A smoother transition can be provided by designing the distal portion of the stiff, preferably metallic, tube so that the flexibility of the stiff, preferably metallic, tube increases toward its distal end.

The discussion that follows focuses on proximal guidewire tube 21. However, it is to be understood that the discussion applies equally well to proximal inflation tube 31, proximal shaft 110, proximal shaft 210 and any stiff tube in a medical device where it is desirable for one end of that tube to be more flexible than the other end.

One means of increasing the flexibility of the distal portion of proximal guidewire tube 21 is to perforate the distal portion of proximal guidewire tube 21 as seen in FIG. 1 to create a transition zone that is more flexible than the proximal portion of proximal guidewire tube 21. The perforations preferably extend along the distal most two to three inches (5.08 to 7.62 cm) of proximal guidewire tube 21. Of course, the transition zone could be longer or shorter as desired. The exact shape, size, depth, spacing and pattern of these perforations should be chosen to increase the flexibility and minimize stress and material fatigue to the distal portion of proximal guidewire tube 21 without compromising its structural integrity or promoting kinking in that region.

One important factor that helps to identify whether these characteristics are met is by analyzing the area moments of inertia of incremental cross sections of proximal guidewire tube 21 perpendicular to its longitudinal axis. The area moment of inertia is defined as $$\int Y^2 dA$$

where Y is the distance to the longitudinal axis and A is the area. This area moment of inertia can be reduced by reducing the cross-sectional area of proximal guidewire tube 21. Reducing the area moment of inertia decreases the stiffness of proximal guidewire tube 21 at that point. Preferably the area moments of inertia should decrease gradually, not abruptly. In addition, the area moments of inertia taken through substantially the entire length of the transition zone should be less than the area moments of inertia taken along the proximal portion of proximal guidewire tube 21. This ensures that the stiffness of proximal guidewire tube 21 gradually decreases to approach the stiffness of distal guidewire tube 22.

Another important factor to help identify whether proximal guidewire tube 21 has the appropriate characteristics to be used in a balloon dilatation catheter is the location of the centroid for the cross-section defined above in connection with the area moment of inertia. Preferably this centroid should be at or close to the longitudinal axis of proximal guidewire tube 21.

One particularly preferred configuration for the transition zone of proximal guidewire tube 21 is to have the perforations arranged in rows with two perforations in each row. One perforation in each row should be located 180° from the other perforation in that row. Each perforation in one row is offset from the perforations in the adjacent rows by 90° and extend at least partially into the space between the perforations in an adjacent row. Preferably the center to center distance between perforations in adjacent rows is 0.005 inches to 0.080 inches (0.13 mm to 2.03 mm). This configuration ensures that throughout the majority of the length of the transition zone, there are no complete annular bands of proximal guidewire tube 21 defining a region with an area moment of inertia equal to the area moment of inertia of a cross section of proximal guidewire tube 21 taken along the proximal portion of proximal guidewire tube 21. Preferably, an annular band is left at the very distal end of proximal guidewire tube 21 for structural integrity. The perforations in every other row are aligned with each other along the longitudinal axis of proximal guidewire tube 21. Where proximal guidewire tube 21 has an outer diameter of 0.025 inches (0.64 mm) each perforation preferably has a length (L) of 0.010 inches to 0.090 inches (0.25 mm to 2.29 mm). In addition, the distance (D) between the centers of each longitudinally aligned perforation is preferably 0.010 inches to 0.090 inches (0.25 mm to 2.29 mm). Distance D could also vary along the rows of the perforations.

Each perforation is formed by electrodischarge machining. In this procedure, guidewire tube 21 is held in place and positioned with respect to the electrodischarge machine electrode to form the perforations. The electrode moves toward guidewire tube 21 at an angle of 30° to 60° to the longitudinal axis of proximal guidewire tube 21. The electrode extends to a depth (Y) of 0.001 inches to 0.012 inches (0.025 mm to 0.30 mm) before being pulled away from the longitudinal axis of guidewire tube 21 at an angle of 30° to 60°. The resulting perforation has a beveled edge. Guidewire tube 21 is then rotated or moved along its longitudinal axis so another perforation can be formed. The perforations in the distal-most row are formed by pulling the electrode in the electrodischarge machine away from proximal guidewire tube 21 at a 90° angle to the longitudinal axis of proximal guidewire tube 21. The depth (Y) of the perforations is less along the most proximal eight rows of perforations.

Figures 6, 7, 8:
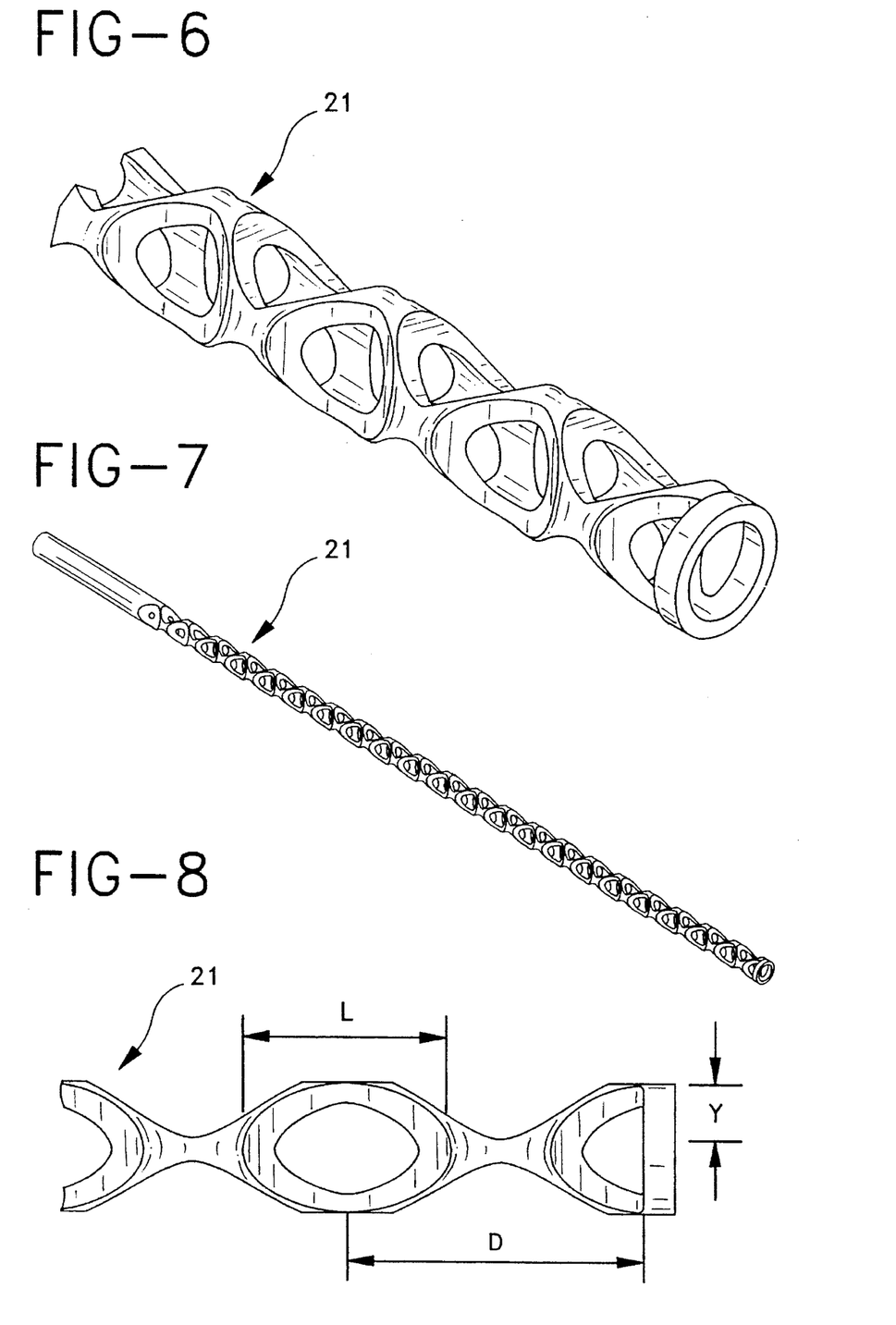
FIG. 6 is an enlarged perspective view of the transition zone of the proximal inner tube of FIG. 1.
FIG. 7 is a perspective view of the proximal inner tube of FIG. 1.
FIG. 8 is a side elevation view of a portion of the transition zone of FIG. 6.
Figure 10:
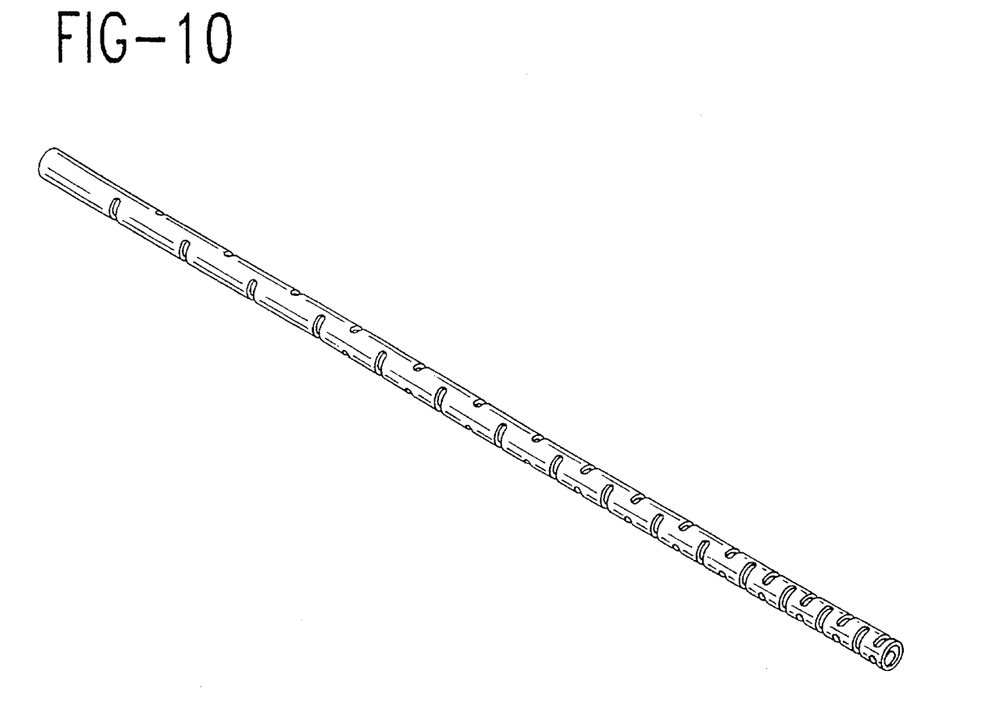
FIGS. 10 through 14 are perspective views of variations of the stiff proximal tube of this invention.

It is also possible to form the perforations into shapes, such as ovals, circles, rectangles or triangles which do not have beveled edges. These shapes may be formed by only moving the electrodischarge machine electrode toward and away from proximal guidewire tube 21 at an angle of 90° to the longitudinal axis. These perforations can be arranged in rows as shown in FIG. 10. Each row contains two perforations on opposite sides of proximal guidewire tube 21, i.e. they are 180 degrees apart. Each perforation in one row is offset from the perforations in the adjacent row by 90°. The perforations in every other row are aligned with each other along the longitudinal axis of guidewire tube 21. In addition, the spacing between adjacent rows of perforations gradually decreases in the distal direction. Thus proximal guidewire tube 21 increases in flexibility in the distal direction. Although not shown, it is to be understood that these perforations could also be arranged as shown in FIG. 7.

Figure 11:
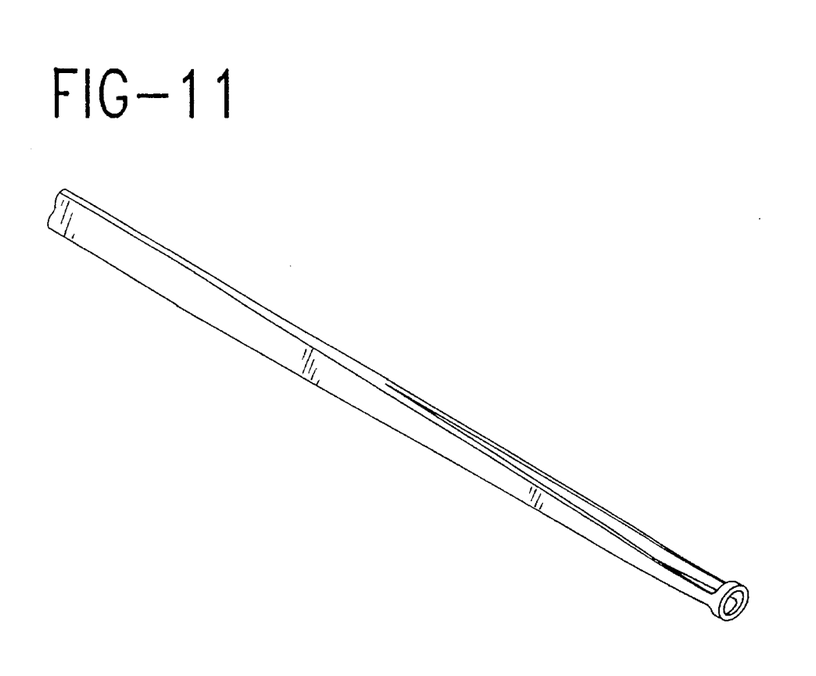
Figure 12:
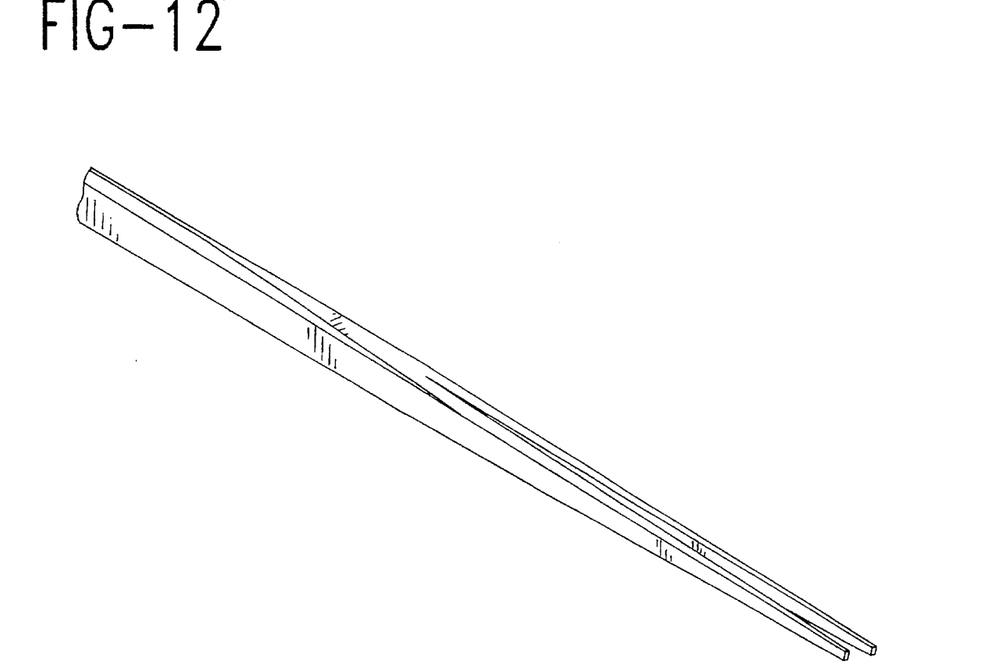
Figure 13:
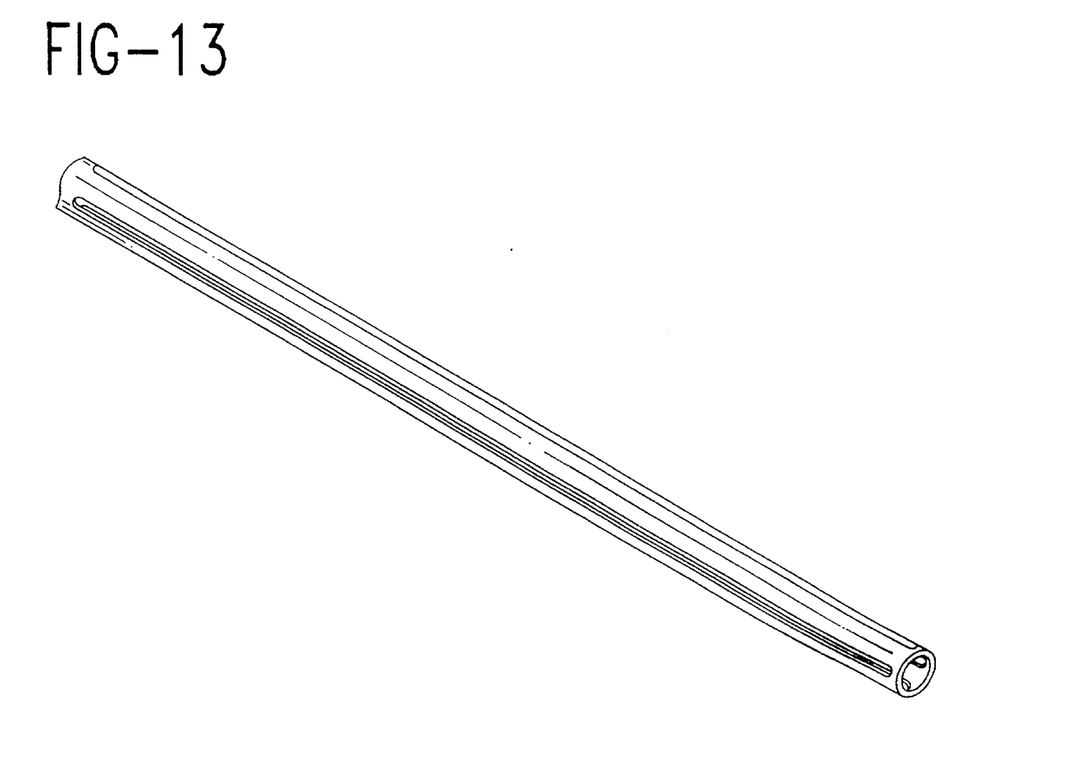
Figure 14:
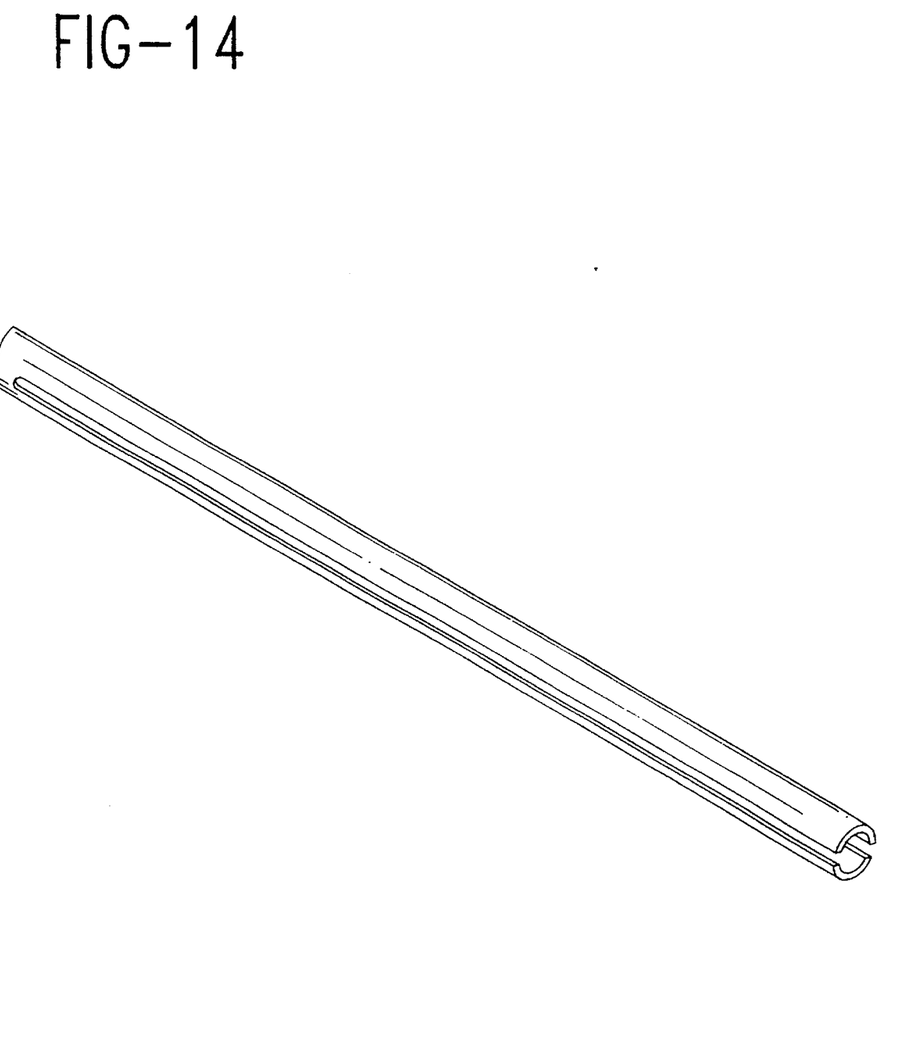

Another embodiment of this invention includes the use of one or more slots cut into the distal portion of proximal guidewire tube 21. See FIGS. 10–14. Any number of slots could be located around the circumference of guidewire tube 21. These slots can also be tapered so that they increase in the distal direction. For example, the embodiment shown in FIG. 11 uses two slots on opposite sides of the distal portion of guidewire tube 21 that gradually increase in size to a point just proximal of the distal end of guidewire tube 21. This leaves an annular ring at the distal end of guidewire tube. Alternatively, the slots could extend to the very distal end of guidewire tube 21 so there would be no annular ring. See FIG. 13. In addition, instead of being tapered, the slots could have a uniform width or could be wavy. Again these slots could extend to the very distal end of guidewire tube 21 as in FIG. 14, or could terminate just short of the distal end to leave an annular ring as in FIG. 13. The embodiment of FIG. 13 also shows a different number of slots. Moreover the slots could each have various lengths.

The perforations and slots described above can be formed by any standard method. For example, electrodischarge machining, chemical etching, mechanical cutting or grinding, or the use of an eximer laser could provide the desired configuration for the stiff, preferably metallic, tube.

It is to be understood that the above description concerning the distal portion of proximal guidewire tube 21 can be applied to the entire length of proximal guidewire tube 21 or any other length to increase the flexibility of that portion of proximal guidewire tube 21. This description can also apply to any stiff, preferably metallic, tube of any type of medical device where a smooth transition is needed between a stiff portion and a more flexible portion.

The proximal portion of distal guidewire tube 22 is connected to the distal end of proximal guidewire tube 21. In order to make guidewire tube 20 fluid tight, a tube must cover the perforations formed in the distal portion of proximal guidewire tube 21. The proximal end of distal guidewire tube 22 is placed against the distal end of proximal guidewire tube 21. A sleeve that is formed of the same material used to form distal guidewire tube 22 is placed over the transition zone of proximal guidewire tube 21 and the proximal portion of distal guidewire tube 22. The sleeve is chemically bonded to proximal guidewire tube 21. In addition, the polymeric tube is heated to bond it to distal guidewire tube 22. This heating also melts the plastic of the sleeve so it extends into the depth of the perforations for a stronger bond between the sleeve and proximal guidewire tube 21. The plastic filled perforations facilitate guidewire movement through proximal guidewire tube 21 because the guidewire would not extend into any of the perforations. In addition, the fatigue resistance and stiffness of the transition zone increases when the perforations are filled with the plastic.

Thus it is seen that a catheter is provided that has a small profile, a flexible distal portion, a stiff proximal portion and a smooth transition from a stiff proximal portion to a flexible distal portion which avoids areas of high stress concentration. One skilled in the art will appreciate that the described embodiments are presented for purposes of illustration and not of limitation and the present invention is only limited by the claims which follow.

I claim:

1. A catheter comprising:

(a) an inner tube; and (b) an outer tube positioned around the inner tube and forming a lumen between the outer tube and inner tube, the outer tube comprising:
  (i) a proximal section having a distal portion, the distal portion having a substantially circular and uninterrupted cross-section throughout its length and a first flexibility;
  (ii) a distal section having a proximal portion, the proximal portion having a substantially circular and uninterrupted cross-section throughout its length and a second flexibility; and
  (iii) a transition section intermediate the proximal section and the distal section, the transition section having one or more openings therein, with the transition section being configured to provide a flexibility which is greater than the first flexibility of the distal portion of the proximal section and which flexibility is less than the second flexibility of the proximal portion of the distal section.

2. The catheter of claim 1 wherein the transition section is metallic.

3. A catheter comprising:
(a) an inner tube comprising
  (i) a non-perforated proximal section having a distal end with a first flexibility;
  (ii) a non-perforated distal section having a proximal end with a second flexibility; and
  (iii) a transition section intermediate the proximal section and the distal section, the transition section having one or more openings therein, with the transition section being configured to provide a flexibility which is greater than the first flexibility of the distal end of the proximal section and which flexibility is less than the second flexibility of the proximal end of the distal section; and
b) an outer tube having a continuous surface positioned in co-axial relation about and bonded to the transition section.

4. The catheter of claim 3 wherein the transition section is metallic.

5. The catheter of claim 4 wherein one or more of the openings have beveled edges.

6. The catheter of claim 3 wherein one or more of the openings have beveled edges.

7. The catheter of claim 3 wherein the outer tube is chemically bonded to the transition section.

8. The catheter of claim 3 wherein the outer tube is plastic and extends into a depth of the one or more openings.

9. A catheter comprising:
(a) an inner tube comprising;
  (i) a non-perforated proximal section having a distal end with a first flexibility;
  (ii) a non-perforated distal section having a proximal end with a second flexibility;
  (iii) a transition section intermediate the proximal section and the distal section, the transition section having one or more openings therein, with the transition section being configured to provide a flexibility which is greater than the first flexibility of the distal end of the proximal section and which flexibility is less than the second flexibility of the proximal end of the distal section; and,
  (iv) a sleeve bonded to the transition section; and
b) an outer tube positioned around the inner tube and forming a lumen between the inner tube and outer tube.

10. The catheter of claim 9 wherein the transition section is metallic.

11. The catheter of claim 9 wherein the sleeve is chemically bonded to the transition section.

12. The catheter of claim 9 wherein the sleeve is plastic and extends into a depth of the one or more openings.

13. A balloon dilatation catheter comprising:
(a) an inner tube comprising
  (i) a proximal section having a distal end with a first flexibility;
  (ii) a distal section having a proximal end with a second flexibility; and
  (iii) a transition section intermediate the proximal section and the distal section, the transition section having one or more openings therein, with the transition section being configured to provide a flexibility which is greater than the first flexibility of the distal end of the proximal section and which flexibility is less than the second flexibility of the proximal end of the distal section;
(b) an outer tube positioned around and attached to the inner tube; and
(c) a balloon connected to the outer tube distal to the transition section.

14. The catheter of claim 13 wherein the transition section is metallic.

15. The catheter of claim 14 wherein one or more of the openings have beveled edges.

16. The catheter of claim 13 wherein one or more of the openings have beveled edges.

17. A catheter comprising:
(a) an inner tube; and
(b) an outer tube positioned around the inner tube and forming a lumen between the outer tube and inner tube, the outer tube comprising:
  (i) a non-perforated proximal section having a distal end with a first flexibility;
  (ii) a non-perforated distal section having a proximal end with a second flexibility;
  (iii) a transition section intermediate the proximal section and the distal section, the transition section having one or more openings therein, with the transition section being configured to provide a flexibility which is greater than the first flexibility of the distal end of, the proximal section and which flexibility is less than the second flexibility of the proximal end of the distal section; and,
  (iv) a sleeve bonded to the transition section.

18. The catheter of claim 17 wherein the transition section is metallic.

19. The catheter of claim 17 wherein the sleeve is chemically bonded to the transition section.

20. The catheter of claim 17 wherein the sleeve is plastic and extends into a depth of the one or more openings.

21. A balloon dilatation catheter comprising:
(a) an inner tube; and
(b) an outer tube positioned around the inner tube and forming a lumen between the outer tube and inner tube, the outer tube comprising:
  (i) a proximal section having a distal end with a first flexibility;
  (ii) a distal section having a proximal end with a second flexibility; and,
  (iii) a transition section intermediate the proximal section and the distal section, the transition section having one or more openings therein, with the transition section being configured to provide a flexibility which is greater than the first flexibility of the distal end of the proximal section and which flexibility is less than the second flexibility of the proximal end of the distal section; and (b) a balloon connected to the outer tube distal to the transition section of the outer tube.

22. The catheter of claim 21 wherein the transition section is metallic.

* * * * *